United States Patent
Bekker et al.

(10) Patent No.: US 9,085,783 B2
(45) Date of Patent: Jul. 21, 2015

(54) L-LACTATE PRODUCTION IN CYANOBACTERIA

(75) Inventors: Martijn Bekker, Amsterdam (NL); Maarten Joost Teixeira de Mattos, Amsterdam (NL); Klaas Jan Hellingwerf, Amsterdam (NL)

(73) Assignee: PHOTANOL BV, Amsterdam (NL)

( * ) Notice: Subject to any disclaimer, the term of this patent is extended or adjusted under 35 U.S.C. 154(b) by 240 days.

(21) Appl. No.: 13/643,969

(22) PCT Filed: Apr. 28, 2010

(86) PCT No.: PCT/NL2010/050245
§ 371 (c)(1),
(2), (4) Date: Dec. 3, 2012

(87) PCT Pub. No.: WO2011/136639
PCT Pub. Date: Nov. 3, 2011

(65) Prior Publication Data
US 2013/0071895 A1    Mar. 21, 2013

(51) Int. Cl.
C12P 7/56      (2006.01)
C12N 15/74     (2006.01)
C12N 9/00      (2006.01)
C12N 9/04      (2006.01)

(52) U.S. Cl.
CPC ............. *C12P 7/56* (2013.01); *C12N 9/0006* (2013.01); *C12N 15/74* (2013.01); *C12Y 101/01027* (2013.01)

(58) Field of Classification Search
None
See application file for complete search history.

(56) References Cited

U.S. PATENT DOCUMENTS

2010/0003731 A1*  1/2010  Ito et al. .................. 435/139

FOREIGN PATENT DOCUMENTS

WO    2007/084477 A1    7/2007
WO    2009/078712 A2    6/2009

OTHER PUBLICATIONS

GenBank: M88490.1 (Retrieved from the Internet: <http://www.ncbi.nlm.nih.gov/nucleotide/149423?report=genbank&log$=nuclalign&blast_rank=3&RID=ZH9CP5SD01R>, retrieved on Aug. 23, 2014).*
Eriksson et al. (Mol Cell Biol Res Commun. May 2000;3(5):292-8 [Abstract], Retrieved from the Internet: <http://www.ncbi.nlm.nih.gov/pubmed/10964753>, retrieved on Aug. 23, 2014).*
Sanchez et al. (Lactate Dehydrogenases in Cyanobacteria, Arch. Microbiol. 104, 57--65 (1975)).*
Engels, Verena et al., "The Global Repressor SugR Controls Expression of Genes of Glycolysis and of the L-Lactate Dehydrogenase LdhA in Corynebacterium glutamicum", Journal of Bacteriology, vol. 190, No. 24, Dec. 2008, pp. 8033-8044.
Luesink, Evert J. et al., "Transcriptional activation of the glycolytic las operon and catabolite repression of the gal operon in Lactococcus lactis are mediated by the catabolite control protein CcpA", Molecular Microbiology, Blackwell Science Ltd., vol. 30, No. 4, 1998, pp. 789-798.
Niederholtmeyer, Henrike et al., "Engineering Cyanobacteria to Synthesize and Export Hydrophilic Products", Applied and Environmental Microbiology, American Society for Microbiology, vol. 76, No. 11, 2010, pp. 3462-3466.
Osanai, Takashi et al., "Sugar catabolism regulated by light- and nitrogen-status in the cyanobacterium Synechocystis sp. PCC 6803", Photochemical and Photobiological Sciences, The Royal Society of Chemistry and Owner Societies, vol. 6, 2007, pp. 508-514.
Vijayakumar, J. et al., "Recent Trends in the Production, Purification and Application of Lactic Acid", Chem. Biochem. Eng. Q., vol. 22, No. 2, 2008, pp. 245-264.
International Search Report issued to International Application No. PCT/NL2010/050245, mailed Jul. 30, 2010.

* cited by examiner

*Primary Examiner* — Suzanne M Noakes
*Assistant Examiner* — Jae W Lee
(74) *Attorney, Agent, or Firm* — Hoffman & Baron, LLP

(57) ABSTRACT

A process of producing L-lactate by feeding carbon dioxide to a culture of a cyanobacterial cell and subjecting this culture to light, wherein the cell is capable of expressing a nucleic acid molecule, which upon expression confers on the cell the ability to convert a glycolytic intermediate into L-lactate and wherein aforementioned nucleic acid molecule is under the control of a regulatory system which responds to light or to a change in the concentration of a nutrient in the culture.

16 Claims, 3 Drawing Sheets

SEQUENCE LISTING

<160> NUMBER OF SEQ ID NOS: 13

<210> SEQ ID NO 1
<211> LENGTH: 978
<212> TYPE: DNA
<213> ORGANISM: Lactococcus lactis
<220> FEATURE:
<221> NAME/KEY: CDS
<222> LOCATION: (1)..(978)

<400> SEQUENCE: 1

```
atg gct gat aaa caa cgt aag aaa gtt atc ctt gtt ggt gac ggt gct    48
Met Ala Asp Lys Gln Arg Lys Lys Val Ile Leu Val Gly Asp Gly Ala
1               5                   10                  15 gta ggt tca tca tac gct ttt gcc ctt gtt aac caa gga att gca caa    96
Val Gly Ser Ser Tyr Ala Phe Ala Leu Val Asn Gln Gly Ile Ala Gln
                20                  25                  30 gaa tta ggt att gtt gac ctt ttt aaa gaa aaa act caa ggg gat gca   144
Glu Leu Gly Ile Val Asp Leu Phe Lys Glu Lys Thr Gln Gly Asp Ala
            35                  40                  45 gaa gac ctt tct cat gcc ttg gca ttt aca tca cct aaa aag att tac   192
Glu Asp Leu Ser His Ala Leu Ala Phe Thr Ser Pro Lys Lys Ile Tyr
        50                  55                  60 tct gca gac tac tct gat gca agc gac gct gac ctc gtt gtc ttg act   240
Ser Ala Asp Tyr Ser Asp Ala Ser Asp Ala Asp Leu Val Val Leu Thr
65                  70                  75                  80 tct ggt gct cca caa aaa cca ggt gaa act cgt ctt gac ctt gtt gaa   288
Ser Gly Ala Pro Gln Lys Pro Gly Glu Thr Arg Leu Asp Leu Val Glu
                85                  90                  95 aaa aat ctt cgt att act aaa gat gtt gta act aaa att gtt gct tca   336
Lys Asn Leu Arg Ile Thr Lys Asp Val Val Thr Lys Ile Val Ala Ser
                100                 105                 110 gga ttc aaa gga atc ttc ctc gtt gct gct aac cca gtt gac atc ttg   384
Gly Phe Lys Gly Ile Phe Leu Val Ala Ala Asn Pro Val Asp Ile Leu
            115                 120                 125 aca tac gca act tgg aaa ttc tct ggt ttc cct aaa aac cgt gtt gta   432
Thr Tyr Ala Thr Trp Lys Phe Ser Gly Phe Pro Lys Asn Arg Val Val
        130                 135                 140 ggt tca ggt act tca ctt gat act gca cgt ttc cgt caa gca ttg gct   480
Gly Ser Gly Thr Ser Leu Asp Thr Ala Arg Phe Arg Gln Ala Leu Ala
145                 150                 155                 160 gaa aaa gtt gac gtt gat gct cgt tca atc cac gca tac atc atg ggt   528
Glu Lys Val Asp Val Asp Ala Arg Ser Ile His Ala Tyr Ile Met Gly
                165                 170                 175 gaa cac ggt gac tca gaa ttt gct gtt tgg tca cac gct aac gtt gct   576
Glu His Gly Asp Ser Glu Phe Ala Val Trp Ser His Ala Asn Val Ala
            180                 185                 190 ggt gtt aaa ttg gaa caa tgg ttc caa gaa aat gac tac ctt aac gaa   624
Gly Val Lys Leu Glu Gln Trp Phe Gln Glu Asn Asp Tyr Leu Asn Glu
```

-continued

```
            195                 200                 205
gca aaa atc gtt gaa ttg ttt gag tct gta cgt gat gca gct tac tca    672
Ala Glu Ile Val Glu Leu Phe Glu Ser Val Arg Asp Ala Ala Tyr Ser
    210                 215                 220 atc atc gct aaa aaa ggt gca aca ttc tac ggt gtg gct gta gcc ctt    720
Ile Ile Ala Lys Lys Gly Ala Thr Phe Tyr Gly Val Ala Val Ala Leu
225                 230                 235                 240 gct cgt att act aaa gca att ctt gat gat gaa cat gca gta ctt cct    768
Ala Arg Ile Thr Lys Ala Ile Leu Asp Asp Glu His Ala Val Leu Pro
            245                 250                 255 gta tca gta ttc caa gat gga caa tat ggg gta agc gac tgc tac ctt    816
Val Ser Val Phe Gln Asp Gly Gln Tyr Gly Val Ser Asp Cys Tyr Leu
            260                 265                 270 ggt caa cca gct gta gtt ggt gct gaa ggt gtt gtt aac cca att cac    864
Gly Gln Pro Ala Val Val Gly Ala Glu Gly Val Val Asn Pro Ile His
            275                 280                 285 att cca ttg aac gat gct gaa atg caa aaa atg gaa gct tct gga gct    912
Ile Pro Leu Asn Asp Ala Glu Met Gln Lys Met Glu Ala Ser Gly Ala
        290                 295                 300 caa ttg aaa gct atc atc gat gaa gct ttt gct aaa gaa gaa ttt gct    960
Gln Leu Lys Ala Ile Ile Asp Glu Ala Phe Ala Lys Glu Glu Phe Ala
305                 310                 315                 320 tct gca gtt aaa aac taa                                            978
Ser Ala Val Lys Asn
            325

<210> SEQ ID NO 2
<211> LENGTH: 325
<212> TYPE: PRT
<213> ORGANISM: Lactococcus lactis

<400> SEQUENCE: 2

Met Ala Asp Lys Gln Arg Lys Lys Val Ile Leu Val Gly Asp Gly Ala
1               5                   10                  15

Val Gly Ser Ser Tyr Ala Phe Ala Leu Val Asn Gln Gly Ile Ala Gln
                20                  25                  30

Glu Leu Gly Ile Val Asp Leu Phe Lys Glu Lys Thr Gln Gly Asp Ala
            35                  40                  45

Glu Asp Leu Ser His Ala Leu Ala Phe Thr Ser Pro Lys Lys Ile Tyr
        50                  55                  60

Ser Ala Asp Tyr Ser Asp Ala Ser Asp Ala Asp Leu Val Val Leu Thr
65                  70                  75                  80

Ser Gly Ala Pro Gln Lys Pro Gly Glu Thr Arg Leu Asp Leu Val Glu
                85                  90                  95

Lys Asn Leu Arg Ile Thr Lys Asp Val Val Thr Lys Ile Val Ala Ser
                100                 105                 110

Gly Phe Lys Gly Ile Phe Leu Val Ala Ala Asn Pro Val Asp Ile Leu
            115                 120                 125

Thr Tyr Ala Thr Trp Lys Phe Ser Gly Phe Pro Lys Asn Arg Val Val
        130                 135                 140

Gly Ser Gly Thr Ser Leu Asp Thr Ala Arg Phe Arg Gln Ala Leu Ala
145                 150                 155                 160

Glu Lys Val Asp Val Asp Ala Arg Ser Ile His Ala Tyr Ile Met Gly
                165                 170                 175

Glu His Gly Asp Ser Glu Phe Ala Val Trp Ser His Ala Asn Val Ala
            180                 185                 190

Gly Val Lys Leu Glu Gln Trp Phe Gln Glu Asn Asp Tyr Leu Asn Glu
```

```
            195                 200                 205
Ala Glu Ile Val Glu Leu Phe Glu Ser Val Arg Asp Ala Ala Tyr Ser
            210                 215                 220

Ile Ile Ala Lys Lys Gly Ala Thr Phe Tyr Gly Val Ala Val Ala Leu
225                 230                 235                 240

Ala Arg Ile Thr Lys Ala Ile Leu Asp Asp Glu His Ala Val Leu Pro
                245                 250                 255

Val Ser Val Phe Gln Asp Gly Tyr Gly Val Ser Asp Cys Tyr Leu
            260                 265                 270

Gly Gln Pro Ala Val Val Gly Ala Glu Gly Val Val Asn Pro Ile His
            275                 280                 285

Ile Pro Leu Asn Asp Ala Glu Met Gln Lys Met Glu Ala Ser Gly Ala
            290                 295                 300

Gln Leu Lys Ala Ile Ile Asp Glu Ala Phe Ala Lys Glu Glu Phe Ala
305                 310                 315                 320

Ser Ala Val Lys Asn
            325

<210> SEQ ID NO 3
<211> LENGTH: 305
<212> TYPE: DNA
<213> ORGANISM: Artificial
<220> FEATURE:
<223> OTHER INFORMATION: promoter

<400> SEQUENCE: 3
agcagtttac agaggcgatt tatcggcggg taagactata cagtatcggg aaaaaattaa      60
gaacggtcaa agaatctgga catatcacaa cccacaatct agtattcaaa atccttctgc     120
ctggccttat ttggtcgtat ttacccattg tgcccaaatc cgaccattgt tgccaattat     180
tccccaggta accacggcga tcgccaagga agatttaag tatttttcc cattctccct       240 aatcctgcgg ccaaggagct gggttaacgt tagggcaagt cggatgtcct ggtgtgaccg     300
ggtca                                                                 305

<210> SEQ ID NO 4
<211> LENGTH: 6901
<212> TYPE: DNA
<213> ORGANISM: Artificial
<220> FEATURE:
<223> OTHER INFORMATION: plasmid construct

<400> SEQUENCE: 4
ctaaattgta agcgttaata ttttgttaaa attcgcgtta aatttttgtt aaatcagctc      60
attttttaac cataggccg aaatcggcaa atcccttat aaatcaaaag aatagaccga      120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta atcggaacc ctaaagggag      300 cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg aagggcgat cggtgcgggc ctcttcgcta ttacgccagc tggcgaaagg      540
gggatgtgct gcaaggcgat taagttgggt aacgccaggg ttttcccagt cacgacgttg     600
taaaacgacg gccagtgagc gcgcgtaata cgactcacta tagggcgaat gggtaccgg     660
```

```
gccccccctc gagcccatct gggaagccgc ttccttagat gagtggttgt acaacggtgg    720
tccttaccag ttggtagtat tccacttcct catcggcatt ttctgctaca tgggtcgtca    780
gtgggaactt tcctaccgct taggtatgcg tccttggatt tgtgtggctt actctgcccc    840
cgtatccgct gccaccgccg tattcttgat ctacccatt ggtcaaggct ccttctctga     900
tggtatgccc ttgggtattt ctggtacctt caacttcatg atcgtgttcc aagctgagca    960
caacatcctg atgcacccct tccacatgtt aggtgtggct ggtgtattcg gtggtagctt   1020
gttctccgcc atgcacggtt ccttggtaac ctcctccttg gtgcgtgaaa ccaccgaagt   1080
tgaatcccag aactacggtt acaaattcgg tcaagaagaa gaaacctaca acatcgttgc   1140
cgcccacggc tactttggtc ggttgatctt ccaatatgct tctttcaaca cagccgttc    1200 cttgcacttc ttcttgggtg cttggcctgt aatcggcatc tggttcactg ctatgggtgt   1260
aagcaccatg gcgttcaacc tgaacggttt caacttcaac cagtccatct ggatagcca    1320 aggccgggta atcggcacct gggctgatgt attgaaccga ccaacatcg ttttgaagt     1380 aatgcacgaa cgcaatgccc acaacttccc cctcgactta gcgtctgggg agcaagctcc   1440
tgtggctttg accgctcctg ctgtcaacgg ttaaaagctt gatatcgaat tcaggaggga   1500
aaatcatggc tgataaacaa cgtaagaaag ttatccttgt tggtgacggt gctgtaggtt   1560
catcatacgc ttttgccctt gttaaccaag gaattgcaca agaattaggt attgttgacc   1620
tttttaaaga aaaaactcaa ggggatgcag aagaccttt catgccttg gcatttacat     1680 cacctaaaaa gatttactct gcagactact ctgatgcaag cgacgctgac ctcgttgtct   1740
tgacttctgg tgctccacaa aaaccaggtg aaactcgtct tgaccttgtt gaaaaaaatc   1800
ttcgtattac taaagatgtt gtaactaaaa ttgttgcttc aggattcaaa ggaatcttcc   1860
tcgttgctgc taacccagtt gacatcttga catacgcaac ttggaaattc tctggtttcc   1920
ctaaaaaccg tgttgtaggt tcaggtactt cacttgatac tgcacgtttc cgtcaagcat   1980
tggctgaaaa agttgacgtt gatgctcgtt caatccacgc atacatcatg ggtgaacacg   2040
gtgactcaga atttgctgtt tggtcacacg ctaacgttgc tggtgttaaa ttggaacaat   2100
ggttccaaga aaatgactac cttaacgaag cagaaatcgt tgaattgttt gagtctgtac   2160
gtgatgcagc ttactcaatc atcgctaaaa aaggtgcaac attctacggt gtggctgtag   2220
cccttgctcg tattactaaa gcaattcttg atgatgaaca tgcagtactt cctgtatcag   2280
tattccaaga tggacaatat ggggtaagcg actgctacct tggtcaacca gctgtagttg   2340
gtgctgaagg tgttgttaac ccaattcaca ttccattgaa cgatgctgaa atgcaaaaaa   2400
tggaagcttc tggagctcaa ttgaaagcta tcatcgatga agcttttgct aaagaagaat   2460
ttgcttctgc agttaaaaac taagaattcc tgcagcccgg gaagcttctc gagattctca   2520
tgtttgacag cttatcatcg ataagcttca cgctgccgca agcactcagg gcgcaagggc   2580
tgctaaagga agcggaacac gtagaaagcc agtccgcaga acggtgctg accccgatg    2640 aatgtcagct actgggctat ctggacaagg gaaaacgcaa gcgcaaagag aaagcaggta   2700
gcttgcagtg gcttacatg gcgatagcta gactgggcgg ttttatggac agcaagcgaa    2760
ccggaattgc cagctggggc gccctctggt aaggttggga agccctgcaa agtaaactgg   2820
atggctttct tgccgccaag gatctgatgg cgcagggat caagatctga tcaagagaca    2880
ggatgaggat cgtttcgcat gattgaacaa gatggattgc acgcaggttc tccggccgct   2940
tgggtggaga ggctattcgg ctatgactgg gcacaacaga caatcggctg ctctgatgcc   3000
```

```
gccgtgttcc ggctgtcagc gcaggggcgc ccggttcttt ttgtcaagac cgacctgtcc    3060
ggtgccctga atgaactgca ggacgaggca cgcgggctat cgtggctggc cacgacgggc    3120
gttccttgcg cagctgtgct cgacgttgtc actgaagcgg aagggactga gctgctattg    3180
ggcgaagtgc cggggcagga tctcctgtca tctcaccttg ctcctgccga gaaagtatcc    3240
atcatggctg atgcaatgcg gcggctgcat acgcttgatc cggctacctg cccattcgac    3300
caccaagcga aacatcgcat cgagcgagca cgtactcgga tggaagccgg tcttgtcgat    3360
caggatgatc tggacgaaga gcatcagggg ctcgcgccag ccgaactgtt cgccaggctc    3420
aaggcgcgca tgcccgacgg cgaggatctc gtcgtgaccc atggcgatgc ctgcttgccg    3480
aatatcatgg tggaaaatgg ccgcttttct ggattcatcg actgtggccg gctgggtgtg    3540
gcggaccgct atcaggacat agcgttggct acccgtgata ttgctgaaga gcttggcggc    3600
gaatgggctg accgcttcct cgtgctttac ggtatcgccg ctcccgattc gcagcgcatc    3660
gccttctatc gccttcttga cgagttcttc tgagcgggac tctggggttc gaaatgaccg    3720
accaagcgac gcccaacctg ccatcacgag atttcgattc caccgccgcc ttctatgaaa    3780
ggttgggctt cggaatcgtt tccgggacg ccggctggat gatcctccag cgcggggatc    3840
tcatgctgga gttcttcgcc caccccgggg gatccttcct tggtgtaatg ccaactgaat    3900
aatctgcaaa ttgcactctc cttcaatggg gggtgctttt tgcttgactg agtaatcttc    3960
tgattgctga tcttgattgc catcgatcgc cggggagtcc ggggcagtta ccattagaga    4020
gtctagagaa ttaatccatc ttcgatagag gaattatggg ggaagaacct gtgccggcgg    4080
ataaagcatt aggcaagaaa ttcaagaaaa aaaatgcctc ctggagcatt gaagaaagcg    4140
aagctctgta ccgggttgag gcctgggggg caccttattt tgccattaat gccgctggta    4200
acataaccgt ctctcccaac ggcgatcggg cggttcgtt agatttgttg gaactggtgg    4260
aagccctgcg gcaaagaaag ctcggcttac ccctattaat tcgttttcc gatattttgg    4320
ccgatcgcct agagcgattg aatagttgtt ttgccaaggc gatcgcccgt tacaattacc    4380
ccaacaccta tcaggcggtt tatccggtca aatgtaacca gcaacgacat ctggtggaag    4440
ccctggttcg ctttgggcaa acttccagt gtggattgga ggcaggttcc aaaccggaat    4500
tgatgattgc cctcgcaact ctaccacctc ccttagaccg tcaggacaag cataccaagc    4560
ccctaatcat ttgtaatggc tacaaagacc aggattatct agaaacagct ctgttagcca    4620
aacgcttagg ccatcgtccc atcatcatca ttgaacaact acgggaactg gaatgggcgg    4680
ccgccaccgc ggtggagctc cagcttttgt tccctttagt gagggttaat tgcgcgcttg    4740
gcgtaatcat ggtcatagct gtttcctgtg tgaaattgtt atccgctcac aattccacac    4800
aacatacgag ccggaagcat aaagtgtaaa gcctggggtg cctaatgagt gagctaactc    4860
acattaattg cgttgcgctc actgcccgct ttccagtcgg gaaacctgtc gtgccagctg    4920
cattaatgaa tcggccaacg cgcggggaga ggcggtttgc gtattgggcg ctcttccgct    4980
tcctcgctca ctgactcgct gcgctcggtc gttcggctgc ggcgagcggt atcagctcac    5040
tcaaaggcgg taatacggtt atccacagaa tcagggata cgcaggaaa gaacatgtga    5100
gcaaaaggcc agcaaaggc caggaaccgt aaaaaggccg cgttgctggc gttttttccat    5160
aggctccgcc cccctgacga gcatcacaaa aatcgacgct caagtcagag gtggcgaaac    5220
ccgacaggac tataaagata ccaggcgttt ccccctggaa gctccctcgt gcgctctcct    5280
gttccgaccc tgccgcttac cggatacctg tccgcctttc tcccttcggg aagcgtggcg    5340
ctttctcata gctcacgctg taggtatctc agttcggtgt aggtcgttcg ctccaagctg    5400
```

```
ggctgtgtgc acgaaccccc cgttcagccc gaccgctgcg ccttatccgg taactatcgt    5460
cttgagtcca acccggtaag acacgactta tcgccactgg cagcagccac tggtaacagg    5520
attagcagag cgaggtatgt aggcggtgct acagagttct tgaagtggtg gcctaactac    5580
ggctacacta gaaggacagt atttggtatc tgcgctctgc tgaagccagt taccttcgga    5640
aaaagagttg gtagctcttg atccggcaaa caaaccaccg ctggtagcgg tggttttttt    5700
gtttgcaagc agcagattac gcgcagaaaa aaggatctca agaagatcc tttgatcttt    5760 tctacggggt ctgacgctca gtggaacgaa aactcacgtt aagggatttt ggtcatgaga    5820
ttatcaaaaa ggatcttcac ctagatcctt ttaaattaaa aatgaagttt taaatcaatc    5880
taaagtatat atgagtaaac ttggtctgac agttaccaat gcttaatcag tgaggcacct    5940
atctcagcga tctgtctatt tcgttcatcc atagttgcct gactccccgt cgtgtagata    6000
actacgatac gggagggctt accatctggc cccagtgctg caatgatacc gcgagaccca    6060
cgctcaccgg ctccagattt atcagcaata aaccagccag ccggaagggc cgagcgcaga    6120
agtggtcctg caactttatc cgcctccatc cagtctatta attgttgccg ggaagctaga    6180
gtaagtagtt cgccagttaa tagtttgcgc aacgttgttg ccattgctac aggcatcgtg    6240
gtgtcacgct cgtcgtttgg tatggcttca ttcagctccg gttcccaacg atcaaggcga    6300
gttacatgat cccccatgtt gtgcaaaaaa gcggttagct ccttcggtcc tccgatcgtt    6360
gtcagaagta agttggccgc agtgttatca ctcatggtta tggcagcact gcataattct    6420
cttactgtca tgccatccgt aagatgcttt tctgtgactg gtgagtactc aaccaagtca    6480
ttctgagaat agtgtatgcg gcgaccgagt tgctcttgcc cggcgtcaat acgggataat    6540
accgcgccac atagcagaac tttaaaagtg ctcatcattg gaaaacgttc ttcggggcga    6600
aaactctcaa ggatcttacc gctgttgaga tccagttcga tgtaacccac tcgtgcaccc    6660
aactgatctt cagcatcttt tactttcacc agcgtttctg ggtgagcaaa aacaggaagg    6720
caaaatgccg caaaaaaggg aataagggcg acacggaaat gttgaatact catactcttc    6780
ctttttcaat attattgaag catttatcag ggttattgtc tcatgagcgg atacatattt    6840
gaatgtattt agaaaaataa acaaataggg gttccgcgca catttccccg aaaagtgcca    6900
c                                                                    6901
```

```
<210> SEQ ID NO 5
<211> LENGTH: 371
<212> TYPE: DNA
<213> ORGANISM: Synechocystis PCC6803

<400> SEQUENCE: 5
taattgtatg cccgactatt gcttaaactg actgaccact gaccttaaga gtaatggcgt     60
gcaaggccca gtgatcaatt tcattatttt tcattatttc atctccattg tccctgaaaa    120
tcagttgtgt cgcccctcta cacagcccag aactatggta aaggcgcacg aaaaaccgcc    180
aggtaaactc ttctcaaccc ccaaaacgcc ctctgtttac ccatggaaaa aacgacaatt    240
acaagaaagt aaaacttatg tcatctataa gcttcgtgta tattaacttc ctgttacaaa    300
gctttacaaa actctcatta atcctttaga ctaagtttag tcagttccaa tctgaacatc    360
gacaaataca t                                                         371
```

```
<210> SEQ ID NO 6
<211> LENGTH: 1470
<212> TYPE: DNA
```

```
<213> ORGANISM: Synechocystis PCC6803
<220> FEATURE:
<221> NAME/KEY: CDS
<222> LOCATION: (388)..(1470)

<400> SEQUENCE: 6
taattgtatg cccgactatt gcttaaactg actgaccact gaccttaaga gtaatggcgt      60
gcaaggccca gtgatcaatt tcattatttt tcattatttc atctccattg tccctgaaaa     120
tcagttgtgt cgcccctcta cacagcccag aactatggta aaggcgcacg aaaaaccgcc     180
aggtaaactc ttctcaaccc ccaaaacgcc ctctgtttac ccatggaaaa acgacaatt      240 acaagaaagt aaaacttatg tcatctataa gcttcgtgta tattaacttc ctgttacaaa     300
gctttacaaa actctcatta atcctttaga ctaagtttag tcagttccaa tctgaacatc     360
gacaaataca taaggaatta taaccaa atg aca acg act ctc caa cag cgc gaa     414
                                Met Thr Thr Thr Leu Gln Gln Arg Glu
                                1               5 agc gct tcc ttg tgg gaa cag ttt tgt cag tgg gtg acc tct acc aac      462
Ser Ala Ser Leu Trp Glu Gln Phe Cys Gln Trp Val Thr Ser Thr Asn
 10              15                  20                  25 aac cgg att tat gtc ggt tgg ttc ggt acc ttg atg atc ccc acc ctc      510
Asn Arg Ile Tyr Val Gly Trp Phe Gly Thr Leu Met Ile Pro Thr Leu
                 30                  35                  40 tta act gcc acc act tgc ttc atc att gcc ttc atc gcc gct ccc ccc      558
Leu Thr Ala Thr Thr Cys Phe Ile Ile Ala Phe Ile Ala Ala Pro Pro
             45                  50                  55 gtt gac atc gac ggt atc cgt gag ccc gtt gct ggt tct ttg ctt tac      606
Val Asp Ile Asp Gly Ile Arg Glu Pro Val Ala Gly Ser Leu Leu Tyr
         60                  65                  70 ggt aac aac atc atc tct ggt gct gtt gta cct tct tcc aac gct atc      654
Gly Asn Asn Ile Ile Ser Gly Ala Val Val Pro Ser Ser Asn Ala Ile
 75                  80                  85 ggt ttg cac ttc tac ccc atc tgg gaa gcc gct tcc tta gat gag tgg      702
Gly Leu His Phe Tyr Pro Ile Trp Glu Ala Ala Ser Leu Asp Glu Trp
 90                  95                 100                 105 ttg tac aac ggt ggt cct tac cag ttg gta gta ttc cac ttc ctc atc      750
Leu Tyr Asn Gly Gly Pro Tyr Gln Leu Val Val Phe His Phe Leu Ile
                110                 115                 120 ggc att ttc tgc tac atg ggt cgt cag tgg gaa ctt tcc tac cgc tta      798
Gly Ile Phe Cys Tyr Met Gly Arg Gln Trp Glu Leu Ser Tyr Arg Leu
            125                 130                 135 ggt atg cgt cct tgg att tgt gtg gct tac tct gcc ccc gta tcc gct      846
Gly Met Arg Pro Trp Ile Cys Val Ala Tyr Ser Ala Pro Val Ser Ala
        140                 145                 150 gcc acc gcc gta ttc ttg atc tac ccc att ggt caa ggc tcc ttc tct      894
Ala Thr Ala Val Phe Leu Ile Tyr Pro Ile Gly Gln Gly Ser Phe Ser
    155                 160                 165 gat ggt atg ccc ttg ggt att tct ggt acc ttc aac ttc atg atc gtg      942
Asp Gly Met Pro Leu Gly Ile Ser Gly Thr Phe Asn Phe Met Ile Val
170                 175                 180                 185 ttc caa gct gag cac aac atc ctg atg cac ccc ttc cac atg tta ggt      990
Phe Gln Ala Glu His Asn Ile Leu Met His Pro Phe His Met Leu Gly
                190                 195                 200 gtg gct ggt gta ttc ggt ggt agc ttg ttc tcc gcc atg cac ggt tcc     1038
Val Ala Gly Val Phe Gly Gly Ser Leu Phe Ser Ala Met His Gly Ser
            205                 210                 215 ttg gta acc tcc tcc ttg gtg cgt gaa acc acc gaa gtt gaa tcc cag     1086
Leu Val Thr Ser Ser Leu Val Arg Glu Thr Thr Glu Val Glu Ser Gln
        220                 225                 230
```

-continued

| | | | | | | | | | | | | | | | | |
|---|---|---|---|---|---|---|---|---|---|---|---|---|---|---|---|---|
| aac | tac | ggt | tac | aaa | ttc | ggt | caa | gaa | gaa | gaa | acc | tac | aac | atc | gtt | 1134 |
| Asn | Tyr | Gly | Tyr | Lys | Phe | Gly | Gln | Glu | Glu | Glu | Thr | Tyr | Asn | Ile | Val | |
| 235 | | | | 240 | | | | | 245 | | | | | | | |
| gcc | gcc | cac | ggc | tac | ttt | ggt | cgg | ttg | atc | ttc | caa | tat | gct | tct | ttc | 1182 |
| Ala | Ala | His | Gly | Tyr | Phe | Gly | Arg | Leu | Ile | Phe | Gln | Tyr | Ala | Ser | Phe | |
| 250 | | | | 255 | | | | | 260 | | | | | 265 | | |
| aac | aac | agc | cgt | tcc | ttg | cac | ttc | ttc | ttg | ggt | gct | tgg | cct | gta | atc | 1230 |
| Asn | Asn | Ser | Arg | Ser | Leu | His | Phe | Phe | Leu | Gly | Ala | Trp | Pro | Val | Ile | |
| | | | 270 | | | | | 275 | | | | | 280 | | | |
| ggc | atc | tgg | ttc | act | gct | atg | ggt | gta | agc | acc | atg | gcg | ttc | aac | ctg | 1278 |
| Gly | Ile | Trp | Phe | Thr | Ala | Met | Gly | Val | Ser | Thr | Met | Ala | Phe | Asn | Leu | |
| | | | 285 | | | | | 290 | | | | | 295 | | | |
| aac | ggt | ttc | aac | ttc | aac | cag | tcc | atc | ttg | gat | agc | caa | ggc | cgg | gta | 1326 |
| Asn | Gly | Phe | Asn | Phe | Asn | Gln | Ser | Ile | Leu | Asp | Ser | Gln | Gly | Arg | Val | |
| | | 300 | | | | | 305 | | | | | 310 | | | | |
| atc | ggc | acc | tgg | gct | gat | gta | ttg | aac | cga | gcc | aac | atc | ggt | ttt | gaa | 1374 |
| Ile | Gly | Thr | Trp | Ala | Asp | Val | Leu | Asn | Arg | Ala | Asn | Ile | Gly | Phe | Glu | |
| | 315 | | | | 320 | | | | | 325 | | | | | | |
| gta | atg | cac | gaa | cgc | aat | gcc | cac | aac | ttc | ccc | ctc | gac | tta | gcg | tct | 1422 |
| Val | Met | His | Glu | Arg | Asn | Ala | His | Asn | Phe | Pro | Leu | Asp | Leu | Ala | Ser | |
| 330 | | | | 335 | | | | | 340 | | | | | 345 | | |
| ggg | gag | caa | gct | cct | gtg | gct | ttg | acc | gct | cct | gct | gtc | aac | ggt | taa | 1470 |
| Gly | Glu | Gln | Ala | Pro | Val | Ala | Leu | Thr | Ala | Pro | Ala | Val | Asn | Gly | | |
| | | | 350 | | | | | 355 | | | | | 360 | | | |

<210> SEQ ID NO 7
<211> LENGTH: 360
<212> TYPE: PRT
<213> ORGANISM: Synechocystis PCC6803

<400> SEQUENCE: 7

Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
            20                  25                  30

Phe Gly Thr Leu Met Ile Pro Thr Leu Leu Ala Thr Thr Cys Phe
        35                  40                  45

Ile Ile Ala Phe Ile Ala Ala Pro Pro Val Asp Ile Asp Gly Ile Arg
    50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

```
Ser Leu Phe Ser Ala Met His Gly Ser Leu Val Thr Ser Ser Leu Val
    210                 215                 220

Arg Glu Thr Thr Glu Val Glu Ser Gln Asn Tyr Gly Tyr Lys Phe Gly
225                 230                 235                 240

Gln Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360

<210> SEQ ID NO 8
<211> LENGTH: 45
<212> TYPE: DNA
<213> ORGANISM: Artificial
<220> FEATURE:
<223> OTHER INFORMATION: primer

<400> SEQUENCE: 8
gcggaattcg cggccgcttc tagagtaatt gtatgcccga ctatt          45

<210> SEQ ID NO 9
<211> LENGTH: 49
<212> TYPE: DNA
<213> ORGANISM: Artificial
<220> FEATURE:
<223> OTHER INFORMATION: primer

<400> SEQUENCE: 9
gtactgcagc ggccgctact agtaatgtat ttgtcgatgt tcagattgg      49

<210> SEQ ID NO 10
<211> LENGTH: 37
<212> TYPE: DNA
<213> ORGANISM: Artificial
<220> FEATURE:
<223> OTHER INFORMATION: primer

<400> SEQUENCE: 10
tttactcgag tgttgtacct tcttccaacg ctatcgg                   37

<210> SEQ ID NO 11
<211> LENGTH: 33
<212> TYPE: DNA
<213> ORGANISM: Artificial
<220> FEATURE:
<223> OTHER INFORMATION: primer

<400> SEQUENCE: 11
tttaaagctt ttaaccgttg acagcaggag cgg                       33
```

```
<210> SEQ ID NO 12
<211> LENGTH: 39
<212> TYPE: DNA
<213> ORGANISM: Artificial
<220> FEATURE:
<223> OTHER INFORMATION: primer

<400> SEQUENCE: 12
aaatgaattc aggagggaaa atcatggctg ataaacaac                              39

<210> SEQ ID NO 13
<211> LENGTH: 38
<212> TYPE: DNA
<213> ORGANISM: Artificial
<220> FEATURE:
<223> OTHER INFORMATION: primer

<400> SEQUENCE: 13
aaatgaattc ttagtttta actgcagaag caaattct                                38
```

L-LACTATE PRODUCTION IN CYANOBACTERIA

CROSS-REFERENCE TO RELATED APPLICATIONS

The present application is the National Stage filing of International Application No. PCT/NL2010/050245, filed Apr. 28, 2010, the entire contents of which are incorporated by reference herein.

FIELD OF THE INVENTION

The invention relates to a process of producing an L-lactate produced in the pathway leading to L-lactate by feeding carbon dioxide to a culture of a cyanobacterial cell and subjecting said culture to light, wherein said cell is capable of expressing a nucleic acid molecule wherein the expression of said nucleic acid molecule confers on said cell the ability to convert a glycolytic intermediate such as pyruvate or glyceraldehyde 3-phosphate into L-lactate and wherein expression of said nucleic acid molecule is under the control of a regulatory system which responds to a change in the concentration of a nutrient in said culture. The invention further relates to a cyanobacterial cell for use in this process.

BACKGROUND OF THE INVENTION

Numerous biotechnological processes make use of genetically engineered organisms in order to produce bulk or fine chemicals, proteins or antibiotics. In many cases, increased production has been obtained by improved gene expression and by optimization of growth conditions. In all processes we are aware of, the initial carbon-precursor has been and still is sugar (notably glucose, but many other mono- and polysaccharides are in use) or related organic substrates: solventogenesis (including butanol and ethanol) and organic acid production (e.g. lactic-, citric- or succinic acid) always starts from glucose, which makes it inefficient as the production process uses a high energy initial compound as substrate.

Lactic acid is a naturally occurring organic acid, which has many applications, e.g. it can be used as an acidulant, preservative in the food industry, pharmaceutical, leather and textile industries, as well as a chemical feedstock (Vijayakumar et al. (2008) Chem. Biochem. Eng. Q 22(2):245-264).

Lactic acid can be produced either via chemical synthesis or via microbial fermentation. Currently, most of the lactic acid is produced via microbial fermentation using lactic acid bacteria, although production using filamentous fungi is also known (Vijayakumar et al. vide supra).

However, there is still a need for an alternative and even improved production process of L-lactate, preferably without the need of expensive or complicated starting materials, which process does not have the drawbacks of existing processes.

DESCRIPTION OF THE INVENTION

Energy ultimately comes from the sun and this energy drives photosynthetic process in plants and photoautotrophic bacteria. This knowledge has led to new methods for the synthesis of biochemicals. In essence, these processes employ plants and algal species to reduce $CO_2$ to the level of sugars and cell material. After harvesting, these end products are converted to ethanol by yeast fermentation (in the case of crops) or converted chemically to biofuels (in the case of algae). The overall energy conservation of these methods is highly inefficient and therefore demands large surface areas. In addition, the processes are rather labor-intensive, are demanding with respect to water consumption and affect foodstock prices with adverse consequences for food supplies. A more remotely similar process is based on the conversion of solar energy into hydrogen. Also this process suffers from a severely decreased efficiency.

U.S. Pat. No. 6,699,696 describes a process of producing ethanol by feeding carbon dioxide to a cyanobacterial cell, especially a *Synechococcus* comprising a nucleic acid molecule encoding an enzyme enabling the cell to convert pyruvate into ethanol, subjecting said cyanobacterial cell to sun energy and collecting ethanol. This system has several drawbacks among others the expression system used is temperature sensitive which demands to adapt the production system for such regulation.

WO 2009/078712 describes a process of producing ethanol, propanol, butanol, acetone, 1,3-propanediol, ethylene or D-lactate and where appropriate intermediary compounds in the pathway leading to any of these organic compounds. The process is carried out by feeding carbon dioxide to a culture of cyanobacterial cells and subjecting the culture to light, wherein the cells are capable of expressing a nucleic acid molecule under the control of a regulatory system which responds to a change in the concentration of a nutrient in the culture which confers on the cell the ability to convert a glycolytic intermediate into the above-mentioned organic compounds and/or into intermediary compounds.

The present invention relates to a scalable process for the production of an organic compound suitable as biochemical for large scale plastic production. The invention combines metabolic properties of photoautotrophic and chemoorganotrophic prokaryotes and is based on the employment of recombinant oxyphototrophs with high rates of conversion of Calvin cycle intermediates to a fermentative end product. Its novelty resides in the fact that its core chemical reactions use $CO_2$ as the sole carbon-containing precursor and light (preferably sunlight) as the sole energy source to drive $CO_2$ reduction. Preferably, production is controlled by a nutrient- or light-mediated promoter. Using a nutrient-mediated promoter, production is controlled by a medium component and starts at the most appropriate time, namely at the highest possible cell density. Alternatively, a light-mediated promoter is controlled by light intensity. Whereas in current production processes for biochemicals, organisms are substrate (e.g., crops in ethanol production) or product (e.g., microalgae as biodiesel), here microorganisms are used as highly specialized catalysts for the conversion of $CO_2$ as substrate to a useful end product. These catalysts can be subjected to optimization strategies through physical- and chemical systems-biology approaches. The biochemical background of the invention is more extensively described in example 1 of WO 2009/078712 (herein incorporated by reference). Each aspect of the invention is more extensively described below.

Cyanobacteria

In a first aspect, the invention provides a *Cyanobacterium* capable of expressing a nucleic acid molecule, wherein the expression of said nucleic acid molecule confers on the *Cyanobacterium* the ability to convert a glycolytic intermediate into an L-lactate produced in the pathway leading to L-lactate. Preferably, the nucleic acid molecule is under the control of a regulatory system which responds to a change in the concentration of a nutrient or to light intensity when culturing said *Cyanobacterium*.

In the context of the invention a *Cyanobacterium* or a cyanobacterial cell (also known as a blue-green algae) is a photosynthetic unicellular prokaryote. Examples of Cyanobacteria include the genera *Aphanocapsa, Anabaena, Nostoc, Oscillatoria, Synechococcus, Gloeocapsa, Agmenellum, Scytonema, Mastigocladus, Arthrosprira, Haplosiphon*. A preferred genus is *Synechococcus*. A more preferred species of this genus is a *Synechocystis* species. Even more preferably, the *Synechocystis* is a Pasteur Culture Collection (PCC) 6803 *Synechocystis*, which is a publicly available strain via ATCC for example. A preferred organism used is the phototrophic *Synechocystis* PCC 6803: this is a fast growing *cyanobacterium* with no specific nutritional demands. Its physiological traits are well-documented: it is able to survive and grow in a wide range of conditions. For example, *Synechocystis* sp. PCC 6803 can grow in the absence of photosynthesis if a suitable fixed-carbon source such as glucose is provided. Perhaps most significantly, *Synechocystis* sp. PCC 6803 was the first photosynthetic organism for which the entire genome sequence was determined. In addition, an efficient gene deletion strategy (Shestakov S V et al, (2002), Photosynthesis Research, 73: 279-284 and Nakamura Y et al, (1999), Nucleic Acids Res. 27:66-68) is available for *Synechocystis* sp. PCC 6803, and this organism is furthermore easily transformable via homologous recombination (Grigirieva G A et al, (1982), FEMS Microbiol. Lett. 13: 367-370).

A *Cyanobacterium* as defined herein is capable of converting a glycolytic intermediate into L-lactate as defined herein. A biochemical background of the Cyanobacteria of the invention is given in WO 2009/078712 (see e.g. Example 1 of WO 2009/078712).

A *Cyanobacterium* as defined herein preferably comprises a nucleic acid molecule encoding an enzyme capable of converting a glycolytic intermediate into L-lactate as defined herein. A *Cyanobacterium* is therefore capable of expressing a nucleic acid molecule as defined herein, whereby the expression of a nucleic acid molecule as defined herein confers on the *Cyanobacterium* the ability to convert a glycolytic intermediate into L-lactate as defined herein.

"Converting a glycolytic intermediate into L-lactate" preferably means that detectable amounts of an organic compound are detected in the culture of a *Cyanobacterium* as defined herein cultured in the presence of light and dissolved carbon dioxide and/or bicarbonate ions during at least 1 day using a suitable assay for the organic compound. A preferred concentration of said dissolved carbon dioxide and/or bicarbonate ions is at least the natural occurring concentration at neutral to alkaline conditions (pH 7 to 8) being approximately 1 mM. A more preferred concentration of carbon dioxide and/or bicarbonate ions is higher than this natural occurring concentration. A preferred method to increase the carbon dioxide and/or bicarbonate ions in solution is by enrichment with waste carbon dioxide from industrial plants. The concentration of carbon dioxide in the gas that is sparged into the culture broth may be increased from the equivalent of 0.03% (air) up to 0.2%.

L-lactate is produced within the cell and may spontaneously diffuse into the culture broth. A preferred assay for L-lactate is High Performance Liquid Chromatography (HPLC). A detectable amount for L-lactate is preferably at least 0.1 mM under said culture conditions and using said assay. Preferably, a detectable amount is at least 0.2 mM, 0.3 mM, 0.4 mM, or at least 0.5 mM.

L-lactate as Organic Product

When an organic product to be produced is L-lactate, preferred nucleic acid molecules code for enzymes capable of converting pyruvate into L-lactate, said enzyme comprise a lactate dehydrogenase. Preferred assays for L-lactate are HPLC and enzymatic assays. A detectable amount by HPLC of L-lactate is preferably at least 0.1 mM under said culture conditions as defined earlier herein and using said assay. A detectable amount by enzymatic assays of L-lactate is preferably at least 0.2 mg/l under said culture conditions as defined earlier herein and using said assay. Therefore, in this preferred embodiment, a *Cyanobacterium* comprises a nucleic acid molecule encoding a L-lactate dehydrogenase, preferably a NAD(P)H-dependent L-lactate dehydrogenase (EC 1.1.1.27; also known as ldh, ldhB; preferably from *Lactococcus lactis*, more preferably from *Lactococcus lactis* subsp. *lactis* MG1363)

Accordingly, this preferred embodiment relates to a *Cyanobacterium* capable of expressing at least one nucleic acid molecule, said nucleic acid molecule being represented by a nucleotide sequence, wherein the expression of this nucleotide sequence confers on the cell the ability to convert the glycolytic intermediate pyruvate into L-lactate:

(a) a nucleotide sequence encoding a L-lactate dehydrogenase, wherein said nucleotide sequence is selected from the group consisting of:
  i. nucleotide sequences encoding a L-lactate dehydrogenase, said L-lactate dehydrogenase comprising an amino acid sequence that has at least 40% sequence identity with the amino acid sequence of SEQ ID NO:2.
  ii. nucleotide sequences comprising a nucleotide sequence that has at least 40% sequence identity with the nucleotide sequence of SEQ ID NO:1.
  iii. nucleotide sequences the reverse complementary strand of which hybridizes to a nucleic acid molecule of sequence of (i) or (ii);
  iv. nucleotide sequences the sequences of which differs from the sequence of a nucleic acid molecule of (iii) due to the degeneracy of the genetic code.

Each nucleotide sequence or amino acid sequence described herein by virtue of its identity percentage (at least 40%) with a given nucleotide sequence or amino acid sequence respectively has in a further preferred embodiment an identity of at least 45%, 50%, 55%, 60%, 65%, 70%, 75%, 80%, 85%, 90%, 95%, 98%, 99% or more, and most preferably 100% identity with the given nucleotide or amino acid sequence respectively. In a preferred embodiment, sequence identity is determined by comparing the whole length of the sequences as identified herein.

Each nucleotide sequence encoding an enzyme as described herein may encode either a prokaryotic or an eukaryotic enzyme, i.e. an enzyme with an amino acid sequence that is identical to that of an enzyme that naturally occurs in a prokaryotic or eukaryotic organism. The present inventors have found that the ability of a particular enzyme or to a combination of particular enzymes as defined herein to confer to a Cyanobacterial cell the ability to convert a glycolytic intermediate into L-lactate does not depend so much on whether the enzyme is of prokaryotic or eukaryotic origin. Rather this depends on the relatedness (identity percentage) of the enzyme amino acid sequence or corresponding nucleotide sequence to that of the corresponding identified SEQ ID NO.

Alternatively or in combination with previous preferred embodiments, the invention relates to a further preferred embodiment, wherein at least one enzyme as defined herein is substantially not sensitive towards oxygen inactivation. "Being substantially not sensitive towards oxygen inactivation" preferably means that when such enzyme is expressed in a *Cyanobacterium* as described herein and when this *Cyanobacterium* is cultured in a process of the invention, significant activity of said enzyme is detectable using a specific assay known to the skilled person. More preferably, a significant activity of said enzyme is at least 20% of the activity of the same enzyme expressed in the same *Cyanobacterium* but cultured in the absence of oxygen. Even more preferably, at least 30%, 35%, 40%, 45%, 50%, 55%, 60%, 65%, 70%, 75%, 80%, 85%, 90%, 95% of the activity is detectable. Most preferably, the activity of said enzyme as expressed in a *Cyanobacterium* as described herein and when this *Cyanobacterium* is cultured in the process of the invention is identical with the activity of the same enzyme as expressed in a same *Cyanobacterium* as described herein and when this *Cyanobacterium* is cultured in the absence of oxygen. This is an advantage of the present invention that the *Cyanobacterium* hence obtained is preferably used in a process of the invention wherein oxygen is produced, since it will substantially not affect the activity of the enzymes used herein.

Alternatively or in combination with previous preferred embodiments, the invention relates to a further preferred embodiment wherein, a *Cyanobacterium* as defined herein is a *Cyanobacterium* that has been transformed with a nucleic acid construct comprising a nucleotide sequence encoding an enzyme as defined above depending on the organic product to be produced. A nucleic acid construct comprising a nucleic acid molecule coding for a given enzyme as defined herein will ensure expression of the given nucleic acid molecule, and of the corresponding enzyme in a *Cyanobacterium*. In a more preferred embodiment, a nucleic acid construct comprises more than one nucleic acid molecule, each nucleic acid molecule coding for a given enzyme. In an even more preferred embodiment, a nucleic acid construct comprises two, three, four nucleic acid molecules, each nucleic acid molecule coding for a given enzyme. In a most preferred embodiment, a nucleic acid construct comprises all nucleic acid molecules needed for the conversion of a glycolytic intermediate into L-lactate, each nucleic acid molecule coding for a given enzyme. This most preferred embodiment is illustrated in example 2. In this most preferred embodiment, a nucleic acid construct comprises an expression cassette, said expression cassette comprising each needed nucleic acid molecule. Each nucleic acid molecule is operably linked with other nucleic acid molecule present. Most preferably, a suitable promoter is operably linked with the expression cassette to ensure expression of the nucleic acid molecule in a *Cyanobacterium* as later defined herein.

To this end, a nucleic acid construct may be constructed as described in e.g. U.S. Pat. No. 6,699,696 or U.S. Pat. No. 4,778,759. A *Cyanobacterium* may comprise a single but preferably comprises multiple copies of each nucleic acid construct. A nucleic acid construct may be maintained on a plasmid which is subject to autonomous replication or it may be maintained on a nucleic acid designed for integration into the host chromosome. Suitable plasmid nucleic acid constructs may e.g. be based on the pBluescript from the company Strategene or on any other plasmid. Preferably, however, each nucleic acid construct is integrated in one or more copies into the genome of a cyanobacterial cell. Integration into a cyanobacterial cell's genome may occur at random by illegitimate recombination but preferably a nucleic acid construct is integrated into the *Cyanobacterium* cell's genome by homologous recombination as is well known in the art (U.S. Pat. No. 4,778,759). Homologous recombination occurs preferably at a neutral integration site. A neutral integration site is an integration which is not expected to be necessary for the production process of the invention, i.e for the growth and/or the production of L-lactate as defined herein. A preferred integration site is the nrt operon as illustrated in the examples (Osanai, T., Imamura, S., Asayama, M., Shirai, M., Suzuki, I., Murata, N., Tanaka, K, (2006) Nitrogen induction of sugar catabolic gene expression in *Synechocystis* sp. PCC 6803. *DNA Research* 13, 185-19). Accordingly, in a more preferred embodiment, a cyanobacterial cell of the invention comprises a nucleic acid construct comprising a nucleic acid molecule, said nucleic acid molecule being represented by a nucleotide sequence, said nucleotide sequence being a coding sequence of an enzyme as identified herein. Said cyanobacterial cell is capable of expression of these enzymes. In an even more preferred embodiment, a nucleic acid molecule encoding an enzyme is operably linked to a promoter that causes sufficient expression of a corresponding nucleic acid molecule in a *Cyanobacterium* to confer to a *Cyanobacterium* the ability to convert a glycolytic intermediate into L-lactate. In case of an expression cassette as earlier defined herein, a promoter is upstream of the expression cassette. Accordingly, in a further aspect, the invention also encompasses a nucleic acid construct as earlier outlined herein. Preferably, a nucleic acid construct comprises a nucleic acid molecule encoding an enzyme as earlier defined herein. Nucleic acid molecules encoding an enzyme have been all earlier defined herein.

A promoter that could be used to achieve the expression of a nucleic acid molecule coding for an enzyme as defined herein may be not native to a nucleic acid molecule coding for an enzyme to be expressed, i.e. a promoter that is heterologous to the nucleic acid molecule (coding sequence) to which it is operably linked. Although a promoter preferably is heterologous to a coding sequence to which it is operably linked, it is also preferred that a promoter is homologous, i.e. endogenous to a *Cyanobacterium*. Preferably, a heterologous promoter (to the nucleotide sequence) is capable of producing a higher steady state level of a transcript comprising a coding sequence (or is capable of producing more transcript molecules, i.e. mRNA molecules, per unit of time) than is a promoter that is native to a coding sequence, preferably under conditions where sun light and carbon dioxide are present. A suitable promoter in this context includes both constitutive and inducible natural promoters as well as engineered promoters. A promoter used in a *Cyanobacterium* cell of the invention may be modified, if desired, to affect its control characteristics. A preferred promoter is a PsbA2, as is further outlined below in the next paragraph.

Alternatively or in combination with previous preferred embodiments, the invention relates to a further preferred embodiment, wherein a nucleic acid molecule as defined herein is expressed constitutively and is additionally regulated so as to respond to a change in light intensity (Mohamed, A., Eriksson, J., Osiewacz, H. D., Jansson, C. (1993) Differential expression of the psbA genes in the cyanobacterium *Synechocystis* 6803. *Molecular and General Genetics* 238, 161-168) and (Eriksson J., Salih, G. F., Ghebramedhin, H., Jansson, C. (2000) Deletion Mutagenesis of the psbA2 Region in *Synechocystis* 6803: Identification of a Putative cis Element Involved in Photoregulation. *Molecular Cell Biology Research Communications* 3, 292-298). In a more preferred embodiment, the expression of a nucleic acid molecule is induced when a culture is exposed to higher light intensities such as for example the light intensity of day as compared to the light intensity at night. As exemplified in example 4, this is preferably achieved by using a PsbA2 promoter in a nucleic acid construct comprising a nucleic acid molecule as defined herein. Such promoter is always active at a basal level, hence also under standard low intensity growth light as well as in darkness. During the day (at least irradiance of 250, 260, 270, 280, 290 or 300 $\mu E/m^2/sec$), a *Cyanobacterium* of the invention will grow and produce L-lactate. During the night (less irradiance than 100, 90, 80, 70, 60 or 50 $\mu E/m^2/sec$), a *Cyanobacterium* will not grow and expression of the L-lactate producing enzyme L-lactate dehydrogenase is lowered. When light is present at considerable higher intensities, e.g. at least 250, 260, 270, 280, 290 or 300 µE/m$^2$/sec, as commonly used standard growth light intensities, the PsbA2 promoter is induced. As a consequence, in this process there is more production of L-lactate as defined herein if the cells are exposed to high light intensity, i.e. at least 250, 260, 270, 280, 290 or 300 µE/m$^2$/sec. There is a basal production if cells are kept in darkness or at light intensities below 100, 90, 80, 70, 60 or 50 µE/m$^2$/sec. This production process has several advantages compared to production processes under a constitutive promoter only: a) As with a constitutive promoter the expression of a nucleic acid construct comprising a nucleic acid molecule as defined herein is always active and therefore L-lactate will always be formed; and b) The yield of L-lactate will be improved. Although not wishing to be bound by any theory, this might be due to the fact that high light treatment as defined above results in higher expression of the nucleic acid molecule as defined herein, whereas at the same time the availability of high light provides also a higher carbon flux to the central carbon metabolite pool. The skilled person knows how to assess the intensity of light in such a way that the cultures production is optimized regarding light influx and its carbon balance.

The full promoter of psbA2 (including its light responsive elements) is identified as a region up to −167 bp upstream the start codon of psbA2. (Eriksson J., Salih, G. F., Ghebramedhin, H., Janson, C. (2000) Deletion Mutagenesis of the psbA2 Region in *Synechocystis* 6803: Identification of a Putative cis Element Involved in Photoregulation. *Molecular Cell Biology Research Communications* 3, 292-298). The gene product of psbA2 is the D1 protein of photosystem II (PSII). Its degradation is affected by the rate of PSII photo damage which also stimulates new transcription of psbA2. (Komenda, J., Hassan, H. A. G., Diner, B. A., Debus, R. J., Barber, J., Nixon, P. J. (2000) Degradation of the Photosystem II D1 and D2 proteins in different strains of the cyanobacterium *Synechocystis* PCC 6803 varying with respect to the type and level of psbA transcript. *Plant Molecular Biology* 42 635-645). Over-expression of psbA2 can be achieved by exposure to light intensities above 250 µE/m$^2$/sec for a defined period of time to stimulate synthesis of new transcript of psbA2. (Kommalapati, M., Hwang, H. J., Wang, H. L., Burnap, R. L. (2007) Engineered ectopic expression of the psbA gene encoding the photosystem II D1 protein in *Synechocystis* sp. PCC6803. *Photosynthetic Research* 92 315-325). Preferably, the cells are exposed to light intensities above 250 µE/m$^2$/sec for at least 15 minutes, however they may be exposed longer, such as for hours, for days or for weeks. Preferably, the psbA2 promoter as identified in SEQ ID NO:5 is used or a promoter which has at least 80% identity with the sequence as provided in SEQ ID NO:5.

Alternatively or in combination with previous embodiments, a nucleic acid molecule as defined herein is expressed constitutively and is regulated so as to respond to a change in the concentration of a nutrient when culturing said Cyanobacteria of the invention. Preferably, this is achieved by a promoter, more preferably, the promoter is a SigE controlled promotor of the glyceraldehyde dehydrogenase gene from Synechocystis PCC 6083 as identified in SEQ ID NO:3 (Takashi Osanai, et al, Positive Regulation of Sugar Catabolic Pathways in the *Cyanobacterium Synechocystis* sp. PCC 6803 by the Group 2 sigma Factor SigE. J. Biol. Chem. (2005) 35: 30653-30659) or a promoter which as at least 80% identity with the sequence as provided in SEQ ID NO:3. This promoter is quite advantageous to be used as outlined below in the next paragraph. Alternatively or in combination with previous preferred embodiments, the invention relates to a further preferred embodiment, wherein the expression of a nucleic acid molecule as defined herein is regulated so as to respond to a change in the concentration of a nutrient such as ammonium (Osanai, T., Imamura, S., Asayama, M., Shirai, M., Suzuki, I., Murata, N., Tanaka, K, (2006) Nitrogen induction of sugar catabolic gene expression in *Synechocystis* sp. PCC 6803. *DNA Research* 13, 185-195). In a more preferred embodiment, the expression of a nucleic acid molecule is induced when ammonium concentration is below a given value. This is preferably achieved by using a SigE promoter in a nucleic acid construct comprising a nucleic acid molecule as defined herein. Such promoter is inactive in a first phase of the process when ammonium is present in a concentration which is approximately above 1 mM. In this first phase, a *Cyanobacterium* will grow and not produce any L-lactate as defined herein. When the ammonium source, has been used for growth and its concentration is approximately below 1 mM, the SigE promoter is induced. As a consequence, the process is divided in 2 phases, a first phase where cell numbers increase and a second phase of the production process of the invention, which is characterized by the production of L-lactate as defined herein. This two phased production process has several advantages compared to one phase production processes: a) the growth phase is separated from the production phase and therefore high cell densities can be obtained in a short time b) the yield of L-lactate as defined herein will be improved due to the fact that no carbon flux to growth will occur in the second phase. The skilled person knows how to assess the concentration of a nutrient such as ammonium in the culture.

Method

In a second aspect, the invention relates to a process of producing L-lactate as defined herein by feeding carbon dioxide to a culture of a cyanobacterial cell and subjecting said culture to light, wherein said cell is capable of expressing a nucleic acid molecule, wherein the expression of said nucleic acid molecule confer on the cell the ability to convert a glycolytic intermediate into L-lactate and wherein said nucleic acid molecule is under the control of a regulatory system which responds to a change in the concentration of a nutrient in said culture.

A *Cyanobacterium*, a glycolytic intermediate, L-lactate, a nucleic acid molecule, and a regulatory system have all earlier been defined herein.

In a process of the invention, carbon dioxide is fed to a culture broth of Cyanobacteria. The skilled person knows that the carbon dioxide concentration is dependent from the temperature, the pH and the concentration of carbon dioxide present in the air used. Therefore, this is quite difficult to give an estimation of the concentration of carbon dioxide which is being used. Below, we give estimations of preferred concentrations used. A preferred feeding concentration of carbon dioxide is air enriched to 5% carbon dioxide. A preferred source of carbon dioxide may be the waste gas from an industrial plant.

Usually a process is started with a culture (also named culture broth) of Cyanobacteria having an optical density measured at 660 nm of approximately 0.2 to 2.0 ($OD_{660}$=0.2 to 2) as measured in any conventional spectrophotometer with a measuring path length of 1 cm. Usually the cell number in the culture doubles every 20 hours. A preferred process takes place in a tank with a depth of 30-50 cm exposed to sun light. In a preferred process, the number of cells increases until the source of ammonium is exhausted or below a given value as earlier explained herein, subsequently the production of L-lactate will start. In a preferred embodiment, the light used is natural.

A preferred natural light is sunlight. Daylight (or sunlight) may have an intensity ranged between approximately 500 and approximately 1500 µEinstein/m$^2$/s. In another preferred embodiment, the light used is artificial. Such artificial light may have an intensity ranged between approximately 70 and approximately 800 µEinstein/m$^2$/s. Preferably, the cells are continuously under the light conditions as specified herein. However, the cells may also be exposed to high light intensities (such as e.g. daylight/sunlight) as defined elsewhere herein for a certain amount of time, after which the cells are exposed to a lower light intensity as defined elsewhere herein for a certain amount of time, and optionally this cycle is repeated. In a preferred embodiment, the cycle is the day/night cycle.

In a preferred process, L-lactate is separated from the culture broth. This may be realized continuously with the production process or subsequently to it. Separation may be based on bipolar fractionating electrodialysis, membrane separation and/or precipitation methods. The skilled person will know which separating method is the most appropriate, such as for example as described in U.S. Pat. No. 6,280,985, U.S. Pat. No. 2,350,370, Vijayakumar et al. (2008) Chem. biochem. Eng. Q 22(2):245-264.

Nucleic Acid Molecule and Expression Vector

In a further aspect, the invention relates to a nucleic acid molecule comprising a nucleotide sequence encoding a L-lactate dehydrogenases defined above and wherein the nucleotide sequence is under the control of a regulatory system which responds to light as is earlier defined herein. Preferably, a nucleotide sequence according to the invention is operably linked to a light-regulated promoter, preferably a psbA2 promoter, more preferably a light-regulated promoter that has at least 80% nucleic acid sequence identity with SEQ ID NO: 5, as further defined above.

The invention also relates to an expression vector comprising a nucleic acid molecule of the invention. Preferably, an expression vector comprises a nucleotide sequence encoding a L-lactate dehydrogenase of the invention, which is operably linked to one or more control sequences, which direct the production of the encoded polypeptide in a cyanobacterium and wherein the nucleotide sequence is under the control of a regulatory system which responds to light as is earlier defined herein. An expression vector may be seen as a recombinant expression vector. An expression vector may be any vector which can be conveniently subjected to recombinant DNA procedures and can bring about the expression of a nucleotide sequence encoding a polypeptide of the invention in a cyanobacterium.

General Definitions

Sequence Identity and Similarity

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by various methods, known to those skilled in the art. In a preferred embodiment, sequence identity is determined by comparing the whole length of the sequences as identified herein.

Preferred methods to determine identity are designed to give the largest match between the sequences tested. Methods to determine identity and similarity are codified in publicly available computer programs. Preferred computer program methods to determine identity and similarity between two sequences include e.g. the BestFit, BLASTP, BLASTN, and FASTA (Altschul, S. F. et al., J. Mol. Biol. 215:403-410 (1990), publicly available from NCBI and other sources (BLAST Manual, Altschul, S., et al., NCBI NLM NIH Bethesda, Md. 20894). A most preferred algorithm used is EMBOSS. Preferred parameters for amino acid sequences comparison using EMBOSS are gap open 10.0, gap extend 0.5, Blosum 62 matrix. Preferred parameters for nucleic acid sequences comparison using EMBOSS are gap open 10.0, gap extend 0.5, DNA full matrix (DNA identity matrix).

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Hybridising Nucleic Acid Sequences

Nucleotide sequences encoding the enzymes expressed in the cell of the invention or promoters used in the cell of the invention may also be defined by their capability to hybridise with the nucleotide sequences of SEQ ID NO. 1, 3, or 5, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

Homologous

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically be operably linked to another promoter sequence than in its natural environment. When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as earlier presented. Preferably the region of identity is greater than about 5 bp, more preferably the region of identity is greater than 10 bp. Preferably, two nucleic acid or polypeptides sequences are said to be homologous when they have more than 80% identity.

Heterologous

The term "heterologous" when used with respect to a nucleic acid (DNA or RNA) or protein refers to a nucleic acid or protein (also named polypeptide or enzyme) that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

Operably Linked

As used herein, the term "operably linked" refers to a linkage of polynucleotide elements (or coding sequences or nucleic acid sequence or nucleic acid molecule) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. Operably linked means that the nucleic acid sequences being linked are typically contiguous and, where necessary to join two protein coding regions, contiguous and in reading frame.

Promoter

As used herein, the term "promoter" refers to a nucleic acid fragment that functions to control the transcription of one or more nucleic acid molecules, located upstream with respect to the direction of transcription of the transcription initiation site of the nucleic acid molecule, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most environmental and developmental conditions. An "inducible" promoter is a promoter that is active under environmental or developmental regulation.

Genetic Modifications

For overexpression of an enzyme in a host cells=of the inventions as described above, as well as for additional genetic modification of a host cell=, preferably Cyanobacteria, host cells are transformed with the various nucleic acid constructs of the invention by methods well known in the art. Such methods are e.g. known from standard handbooks, such as Sambrook and Russel (2001) "Molecular Cloning: A Laboratory Manual ($3^{rd}$ edition), Cold Spring Harbor Laboratory, *Cold Spring Harbor Laboratory Press*, or F. Ausubel et al, eds., "Current protocols in molecular biology", Green Publishing and Wiley Interscience, New York (1987). Methods for transformation and genetic modification of cyanobacterial cells are known from e.g. U.S. Pat. No. 6,699,696 or U.S. Pat. No. 4,778,759.

A promoter for use in a nucleic acid construct for overexpression of an enzyme in a cyanobacterial cell of the invention has been described above. Optionally, a selectable marker may be present in a nucleic acid construct. As used herein, the term "marker" refers to a gene encoding a trait or a phenotype which permits the selection of, or the screening for, a Cyanobacterial cell containing the marker. A marker gene may be an antibiotic resistance gene whereby the appropriate antibiotic can be used to select for transformed cells from among cells that are not transformed. Preferably however, a non-antibiotic resistance marker is used, such as an auxotrophic marker (URA3, TRP1, LEU2). In a preferred embodiment, a Cyanobacterial cell transformed with a nucleic acid construct is marker gene free. Methods for constructing recombinant marker gene free microbial host cells are disclosed in EP-A-0 635 574 and are based on the use of bidirectional markers. Alternatively, a screenable marker such as Green Fluorescent Protein, lacZ, luciferase, chloramphenicol acetyltransferase, beta-glucuronidase may be incorporated into a nucleic acid construct of the invention allowing to screen for transformed cells.

Optional further elements that may be present in a nucleic acid construct of the invention include, but are not limited to, one or more leader sequences, enhancers, integration factors, and/or reporter genes, intron sequences, centromers, telomers and/or matrix attachment (MAR) sequences. A nucleic acid construct of the invention can be provided in a manner known per se, which generally involves techniques such as restricting and linking nucleic acids/nucleic acid sequences, for which reference is made to the standard handbooks, such as Sambrook and Russel (2001) "Molecular Cloning: A Laboratory Manual ($3^{rd}$ edition), Cold Spring Harbor Laboratory, *Cold Spring Harbor Laboratory Press*.

Methods for inactivation and gene disruption in Cyanobacterial cells are well known in the art (see e.g. Shestakov S V et al, (2002), Photosynthesis Research, 73: 279-284 and Nakamura Y et al, (1999), Nucleic Acids Res. 27:66-68).

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a peptide or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety. The following examples are offered for illustrative purposes only, and are not intended to limit the scope of the present invention in any way

EXAMPLES

Example 1

Figure 1:
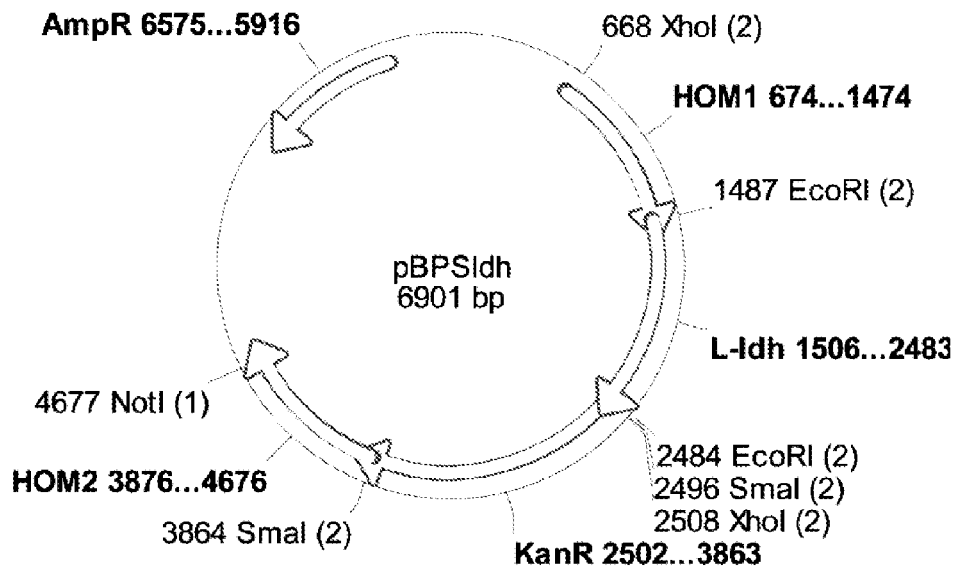
FIG. 1: pBPSldh. The construct represents the transcriptional coupled approach. HOM1 and HOM2 are the integration platforms to facilitate (double) homologous recombination with the respective sequence in the cyanobacterial genome. KanR resulting in kanamycine resistant is used as positive (antibiotic) marker. The plasmid is based on pBluescript (SK+II, Strategene). In SEQ ID NO: 4 the nucleic acid sequence of pBPSldh is given.

Strategy 1. Cloning of the PsbA2 Promoter in Front of a Gene of Interest
Promoter sequence of psbA2 of *Synechocystis* sp. PCC 6803: (SEQ ID NO: 5)

```
TAATTGTATGCCCGACTATTGCTTAAACTGACTGACCACTGACCTTAAG
AGTAATGGCGTGCAAGGCCCAGTGATCAATTTCATTATTTTTCATTATT
TCATCTCCATTGTCCCTGAAAATCAGTTGTGTCGCCCCTCTACACAGCC
CAGAACTATGGTAAAGGCGCACGAAAAACCGCCAGGTAAACTCTTCTCA
ACCCCCAAAACGCCCTCTGTTTACCCATGGAAAAAACGACAATTACAAG
AAAGTAAAACTTATGTCATCTATAAGCTTCGTGTATATTAACTTCCTGT
TACAAAGCTTTACAAAACTCTCATTAATCCTTTAGACTAAGTTTAGTCA
GTTCCAATCTGAACATCGACAAATACAT
```

Sequence derived from cyanobase. The promoter sequence is 371 bp in length and stops right upstream of the Ribosomal Binding Site (RBS). Primer binding sites are underlined. Primers used contain sequences for restriction enzymes for cloning purposes:

| Name | Sequence | SEQ ID NO |
|---|---|---|
| PpsbA2_F | GCGgaattcgcggccgcttctagag TAATTGTATGCCCGACTATT | 8 |
| PpsbA2_R | GTActgcagcggccgctactagta ATGTATTTGTCGATGTTCAGATTGG | 9 |

Strategy 2. Cloning a Gene of Interest Transcriptional Coupled to the psbA2 Gene
Promoter and ORF sequence of psbA2 of Synechocystis sp. PCC 6803 (SEQ ID NO:6; amino acid sequence in SEQ ID NO:7):

```
TAATTGTATGCCCGACTATTGCTTAAACTGACTGACCACTGACCTTAAG
AGTAATGGCGTGCAAGGCCCAGTGATCAATTTCATTATTTTTCATTATT
TCATCTCCATTGTCCCTGAAAATCAGTTGTGTCGCCCCTCTACACAGCC
CAGAACTATGGTAAAGGCGCACGAAAAACCGCCAGGTAAACTCTTCTCA
ACCCCCAAAACGCCCTCTGTTTACCCATGGAAAAAACGACAATTACAAG
AAAGTAAAACTTATGTCATCTATAAGCTTCGTGTATATTAACTTCCTGT
TACAAAGCTTTACAAAACTCTCATTAATCCTTTAGACTAAGTTTAGTCA
GTTCCAATCTGAACATCGACAAATACATAAGGAATTATAACCAAATGAC
AACGACTCTCCAACAGCGCGAAAGCGCTTCCTTGTGGGAACAGTTTTGT
CAGTGGGTGACCTCTACCAACAACCGGATTTATGTCGGTTGGTTCGGTA
CCTTGATGATCCCCACCCTCTTAACTGCCACCACTTGCTTCATCATTGC
CTTCATCGCCGCTCCCCCCGTTGACATCGACGGTATCCGTGAGCCCGTT
GCTGGTTCTTTGCTTTACGGTAACAACATCATCTCTGGTGCTGTTGTAC
CTTCTTCCAACGCTATCGGTTTGCACTTCTACCCCATCGGGAAGCCGC
TTCCTTAGATGAGTGGTTGTACAACGGTGGTCCTTACCAGTTGGTAGTA
TTCCACTTCCTCATCGGCATTTTCTGCTACATGGGTCGTCAGTGGGAAC
TTTCCTACCGCTTAGGTATGCGTCCTTGGATTTGTGTGGCTTACTCTGC
CCCCGTATCCGCTGCCACCGCCGTATTCTTGATCTACCCCATTGGTCAA
GGCTCCTTCTCTGATGGTATGCCCTTGGGTATTTCTGGTACCTTCAACT
TCATGATCGTGTTCCAAGCTGAGCACAACATCCTGATGCACCCCTTCCA
CATGTTAGGTGTGGCTGGTGTATTCGGTGGTAGCTTGTTCTCCGCCATG
CACGGTTCCTTGGTAACCTCCTCCTTGGTGCGTGAAACCACCGAAGTTG
```

```
AATCCCAGAACTACGGTTACAAATTCGGTCAAGAAGAAGAAACCTACAA

CATCGTTGCCGCCCACGGCTACTTTGGTCGGTTGATCTTCCAATATGCT

TCTTTCAACAACAGCCGTTCCTTGCACTTCTTCTTGGGTGCTTGGCCTG

TAATCGGCATCTGGTTCACTGCTATGGGTGTAAGCACCATGGCGTTCAA

CCTGAACGGTTTCAACTTCAACCAGTCCATCTTGGATAGCCAAGGCCGG

GTAATCGGCACCTGGGCTGATGTATTGAACCGAGCCAACATCGGTTTTG

AAGTAATGCACGAACGCAATGCCCACAACTTCCCCCTCGACTTAGCGTC

TGGGGAGCAAGCTCCTGTGGCTTTGACCGCTCCTGCTGTCAACGGTAA
```

Sequence derived from cyanobase. The promoter and gene sequence is 1470 bp in length and stops at the stop codon of psbA2. Primer binding sites are underlined. RBS and start codon (ATG) and stop codon (TAA) are bold and underlined. Primers used contain sequences for restriction enzymes for cloning purposes:

| Name | Sequence | SEQ ID NO: |
|---|---|---|
| Hom1Xho_F | TTTACTCGAGTGTTGTACCTTCTTCC AACGCTATCGG | 10 |
| Hom1Hind_R | TTTAAAGCTTTTAACCGTTGACAGCA GGAGCGG | 11 |

L-ldh is derived from *Lactococcus lactis* MG1363 (SEQ ID NO:1 and 2):

```
Atggctgataaacaacgtaagaaagttatccttgttggtgacggtgctgtaggttcatcatacgcttttgcccttgttaaccaagg aattgcacaagaattaggtattgttgaccttttttaaagaaaaaactcaaggggatgcagaagacctttctcatgccttggcattta catcacctaaaaagatttactctgcagactactctgatgcaagcgacgctgacctcgttgtcttgacttctggtgctccacaaaaa ccaggtgaaactcgtcttgaccttgttgaaaaaaatcttcgtattactaaagatgttgtaactaaaattgttgcttcaggattcaaag gaatcttcctcgttgctgctaacccagttgacatcttgacatacgcaacttggaaattctctggtttccctaaaaaccgtgttgtag gttcaggtacttcacttgatactgcacgtttccgtcaagcattggctgaaaaagttgacgttgatgctcgttcaatccacgcatac atcatgggtgaacacggtgactcagaatttgctgtttggtcacacgctaacgttgctggtgttaaattggaacaatggttccaag aaaatgactaccttaacgaagcagaaatcgttgaattgtttgagtctgtacgtgatgcagcttactcaatcatcgctaaaaaggt gcaacattctacggtgtggctgtagcccttgctcgtattactaaagcaattcttgatgatgaacatgcagtacttcctgtatcagta ttccaagatggacaatatggggtaagcgactgctaccttggtcaaccagctgtagttggtgctgaaggtgttgttaacccaattc acattccattgaacgatgctgaaatgcaaaaaatggaagcttctggagctcaattgaaagctatcatcgatgaagcttttgctaa agaagaatttgcttctgcagttaaaaactaa
```

| Name | Primer | SEQ ID NO: |
|---|---|---|
| LldhRBS_F | AAATGAATTCAGGAGG GAAAATCATGGCTGATAAACAAC | 12 |
| Lldh_R | aaatgaattcttagttttttaact gcagaagcaaattct | 13 |

Example 2

Biochemical Background of the *Cyanobacterium* of the Invention

Figure 2:
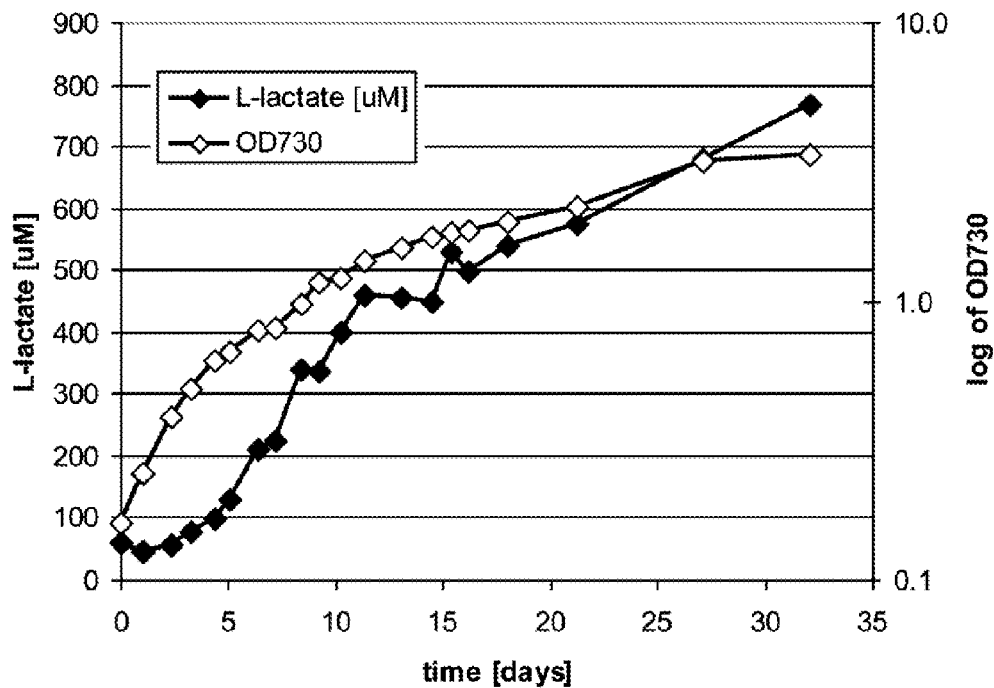
FIG. 2: L-lactate detection in *Synechocystis* $P_{psbA2}$::psbA2::ldh::kan cultures growing in BG-11 depicted on the left Y-axis. OD730 times 100 on the right (log scale) Y-axis.

L-ldh of the organism *L. lactis* (SEQ ID NO:1) is fused downstream to the transcript of psbA2 as described in example 1 above. The plasmid was transformed into *Synechocystis* PCC 6803 (freely obtainable, e.g. from Research Group of Aquatic Microbiology (AMB); Prof. dr. Jef Huisman, Institute for Biodiversity and Ecosystem Dynamics; University of Amsterdam, Amsterdam, The Netherlands; or see publications e.g. Hackenberg et al. (2009) Planta 230(4): 625-637). Mutant cultures were selected for by growth on agar plates containing 20 μg/ml of kanamycine until the genome was fully segregated. This mutant was named *Synechocystis* ldh-8. A scratch of mutant culture was inoculated in BG-11 medium supplemented with 10 mM TES-buffer-NaOH (pH=8.0) and 10 ug/ml kanamycine and grown to stationary phase within several days (OD of 1.5). An aliquot of the initial culture was used to inoculate 100 ml BG-11 supplemented with 10 mM TES-buffer-NaOH (pH=8.0) and with 10 μg/ml kanamycine to an OD of 0.1. The culture was incubated at low light intensity (~40 μE), 30° C. and shaking at 100 rpm. On average every second day 1 ml of culture was collected, processed and L-lactate was determined in 100 μl the cultures supernatant with an enzymatic assay provided by Megazyme (Megazyme International Ireland Ltd. Ireland). With the help of standard concentrations of L-lactate the concentration of L-lactate in the culture was determined (FIG. 2). In conclusion, L-lactate production increases in time (at least up to 30 days) at a rate of more than 20 $\mu mol\cdot(gr\,[dw])^{-1}\cdot h^{-1}$.

Example (3)

Resistance to lactic acid of Synechocystis PCC 6803

Figure 3:
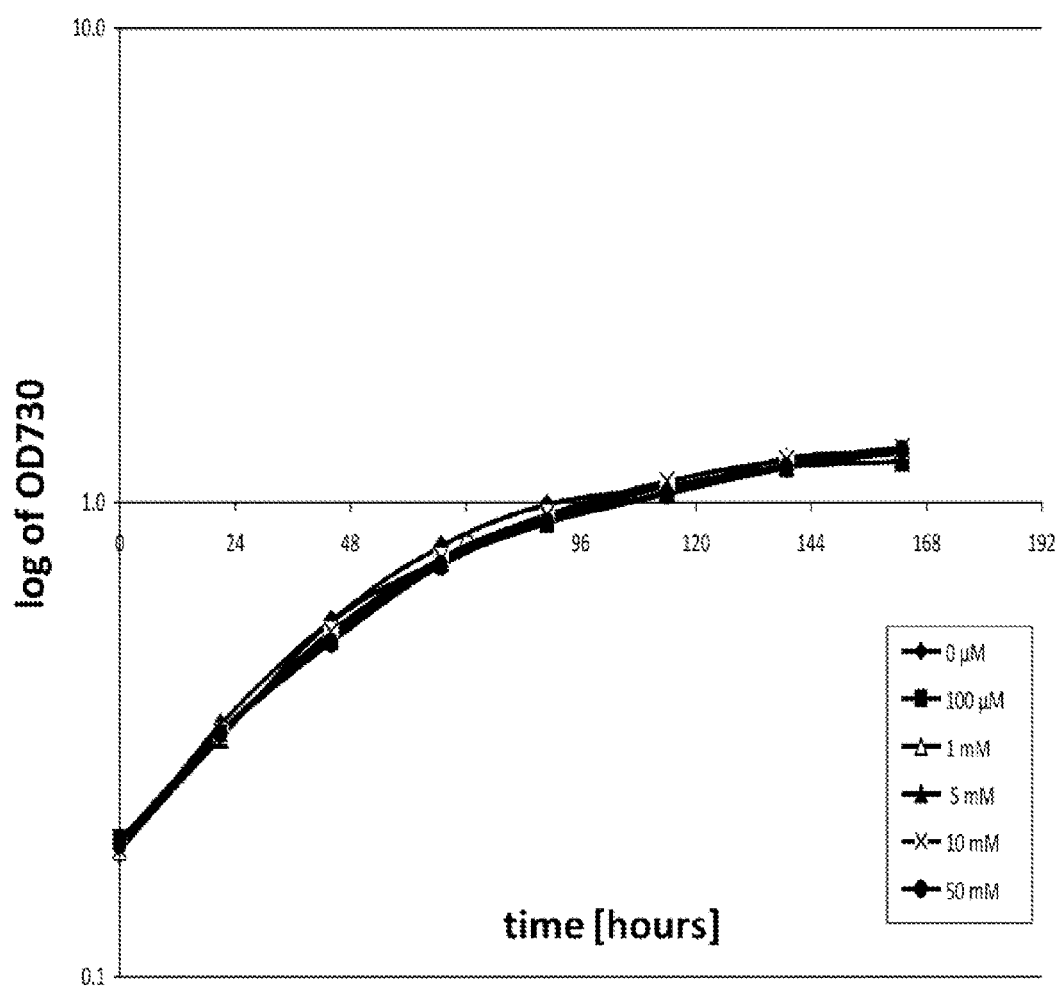
FIG. 3: Growth curve of Synechocystis glucose non-tolerant cultures growing in BG-11 supplemented with 10 mM TES and 5 mM glucose at 37° C.

The culture was grown in 100 ml BG-11 supplemented with 10 mM TES-buffer-NaOH (pH=8.0) and with 10 μg/ml kanamycine to an OD of 0.1. The culture was incubated at low light intensity (~40 μE), 30° C. and shaking at 100 rpm. It was clearly shown (FIG. 3) that up to a concentration of 50 mM L-lactic acid cultures are not affected with respect to growthrate.

Example (4)

Figure 4:
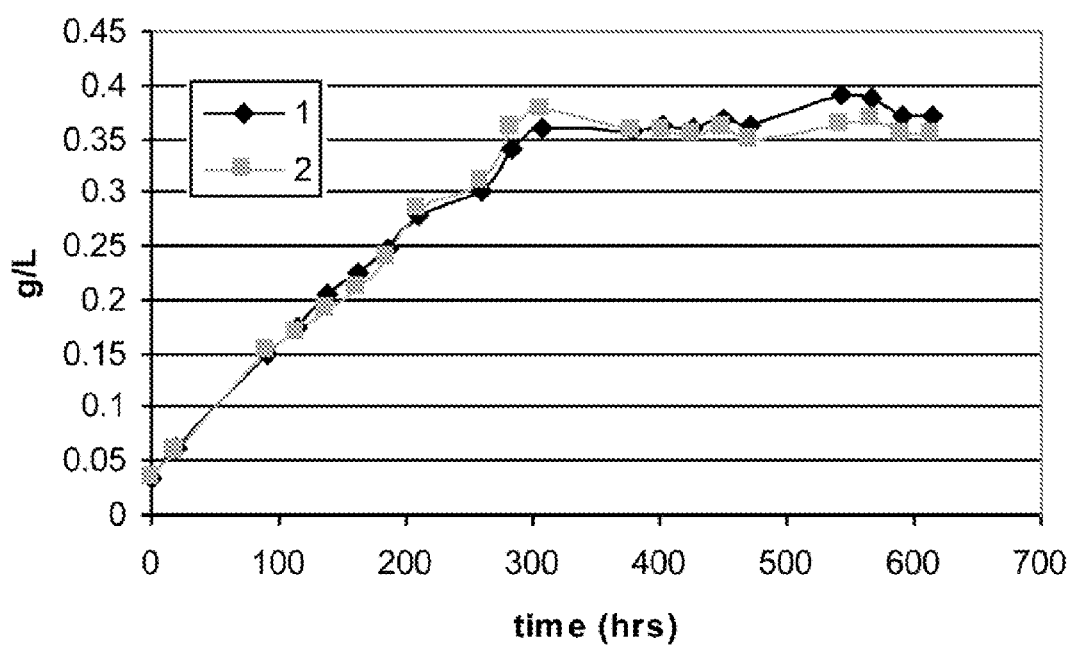
FIG. 4. Growth of Synechocystis ldh-8 in a 1.8 liter continuous growth system. X-axis indicates time in hours, y-axis the cell concentration in gram/liter. 1 and 2 indicate two biological replicates.

Lactate Production Under Control of a psbA Promoter in Synechocystis PCC 6803 in a Continuous Growth Fermentor The lactate producing *Synechocystis* PCC 6803 mutant ldh-8 was grown in a continuous culture with a dilution rate of 0.018 in BG-11 medium with 10 mM $NaNO_3$, 50 mM $NaCO_3$ and 20 mM TES buffer. The culture was mixed by air bubbling with 1% added $CO_2$, and illuminated with continuous white light from a LED-light source at an intensity of ~450 µE. Lactate concentrations were determined with the enzymatic l-lactate assay kit from Megazyme (see FIG. 4).

Duplicate samples were taken after 300 hours and washed in BG-11 medium to remove lactate. Lactate production was monitored in batch cultures of 100 ml with a cell density of 0.33 g/L for 5 hours at a light intensity of 150 µE.

Duplicate samples were also taken after 600 hours and the lactate concentration was determined directly from chemostat. On average the lactate concentration in chemostat was 647 µM, this gives a lactate flux of 647*0.018/0.36=32.3 µmol·(gr $[dw])^{-1}·h^{-1}$. This shows a constant production of L-lactate at a rate of 1 mg/l/hour during at least 3 weeks.

The invention claimed is:

1. A process of producing L-lactate by feeding carbon dioxide to a culture of a cyanobacterial cell and subjecting said culture to light, wherein said cell comprises a nucleic acid molecule encoding an L-lactate dehydrogenase that is not sensitive towards oxygen inactivation, and wherein the expression of said nucleic acid molecule confers on the cell the ability to convert a glycolytic intermediate into L-lactate, wherein the nucleic acid molecule comprises a nucleotide sequence encoding a L-lactate dehydrogenase, and wherein said nucleotide sequence is selected from the group consisting of:
 i. nucleotide sequences encoding a L-lactate dehydrogenase, said L-lactate dehydrogenase comprising an amino acid sequence that has at least 50% sequence identity with the amino acid sequence of SEQ ID NO:2;
 ii. nucleotide sequences comprising a nucleotide sequence that has at least 50% sequence identity with the nucleotide sequence of SEQ ID NO:1;
 iii. nucleotide sequences the reverse complementary strand of which hybridizes to a nucleic acid molecule of a sequence of (i) or (ii); and
 iv. nucleotide sequences the sequences of which differ from the sequence of a nucleic acid molecule of (iii) due to the degeneracy of the genetic code.

2. The process according to claim 1, wherein said nucleic acid molecule is under the control of a regulatory system which responds to light intensity.

3. The process according to claim 1, wherein the nucleic acid molecule comprises a nucleotide sequence encoding a L-lactate dehydrogenase, wherein said nucleotide sequence is selected from the group consisting of:
 i. nucleotide sequences encoding a L-lactate dehydrogenase, said L-lactate dehydrogenase comprising an amino acid sequence that has at least 80% sequence identity with the amino acid sequence of SEQ ID NO:2;
 ii. nucleotide sequences comprising a nucleotide sequence that has at least 80% sequence identity with the nucleotide sequence of SEQ ID NO:1;
 iii. nucleotide sequences the reverse complementary strand of which hybridizes to a nucleic acid molecule of a sequence of (i) or (ii); and
 iv. nucleotide sequences the sequences of which differ from the sequence of a nucleic acid molecule of (iii) due to the degeneracy of the genetic code.

4. The process according to claim 1, wherein the nucleic acid molecule comprised in the cell is integrated into its genome via homologous recombination.

5. The process according to claim 1, wherein the nucleic acid molecule is under the control of a light-regulated promoter.

6. The process according to claim 1, wherein the nucleic acid molecule is under the control of a nutrient-regulated promoter.

7. The process according to claim 1, wherein L-lactate is separated from the culture.

8. The process according to claim 1, wherein the glycolytic intermediate is pyruvate.

9. The process according to claim 1, wherein said nucleic acid molecule is under the control of a regulatory system which responds to a change in the concentration of a nutrient of said culture.

10. The process according to claim 1, wherein the cyanobacterial cell is derived from a *Synechocystis* cell.

11. The process according to claim 1, wherein the cyanobacterial cell is a *Synechocystis* PCC 6803 cell.

12. The process of claim 1, wherein the L-lactate dehydrogenase is NAD(P)H-dependent.

13. The process of claim 5, wherein the light-regulated promoter is a psbA2 promoter.

14. The process of claim 5, wherein the light-regulated promoter is a light-regulated promoter that has at least 80% nucleic acid sequence identity with SEQ ID NO: 5.

15. The process of claim 6, wherein the nutrient-regulated promoter is a SigE promoter.

16. The process of claim 6, wherein the nutrient-regulated promoter is a nutrient-regulated promoter that has at least 80% nucleic acid sequence identity with SEQ ID NO:3.

* * * * *